(12) United States Patent
Wood

(10) Patent No.: US 6,403,369 B1
(45) Date of Patent: Jun. 11, 2002

(54) CELL CULTURE VESSEL

(76) Inventor: Gary W. Wood, 6609 State Line, Kansas City, MO (US) 64113-1807

( * ) Notice: Subject to any disclaimer, the term of this patent is extended or adjusted under 35 U.S.C. 154(b) by 0 days.

(21) Appl. No.: 09/766,202

(22) Filed: Jan. 19, 2001

(51) Int. Cl.$^7$ ................................................. C12M 1/24
(52) U.S. Cl. ................................ 435/304.1; 435/288.1; 435/304.3; 215/40
(58) Field of Search ................................ 422/100, 102; 435/288.1, 304.1, 304.3; 215/40, 306, 315

(56) References Cited

U.S. PATENT DOCUMENTS

| | | | |
|---|---|---|---|
| 3,941,662 A | 3/1976 | Munder et al. | 195/127 |
| 3,946,780 A * | 3/1976 | Sellers | |
| 4,142,940 A | 3/1979 | Modolell et al. | 195/139 |
| 4,770,854 A * | 9/1988 | Lyman | 422/102 |
| 4,829,002 A | 5/1989 | Pattillo et al. | 435/284 |
| 4,889,812 A | 12/1989 | Guinn et al. | 435/289 |
| 4,910,147 A * | 3/1990 | Bacehowski et al. | 45/296 |
| 5,047,347 A | 9/1991 | Cline | 435/296 |
| 5,139,952 A | 8/1992 | Honda et al. | 435/284 |
| 5,151,366 A | 9/1992 | Serkes et al. | 435/285 |
| 5,391,496 A | 2/1995 | Kayal et al. | 435/286 |
| 5,424,209 A | 6/1995 | Kearney | 435/284 |
| 5,565,353 A | 10/1996 | Klebe et al. | 435/240.25 |
| 5,578,591 A | 11/1996 | Burton et al. | 514/210 |
| 5,595,907 A | 1/1997 | Kayal et al. | 435/288.1 |
| 5,650,325 A | 7/1997 | Spielmann | 435/299.1 |
| 5,686,304 A | 11/1997 | Codner | 435/325 |
| 5,686,401 A | 11/1997 | Willey et al. | 510/313 |
| 5,763,261 A | 6/1998 | Gruenberg | 435/286.5 |
| 5,783,440 A | 7/1998 | Stevens | 435/304.3 |
| 5,801,054 A | 9/1998 | Kiel et al. | 435/297.5 |
| 5,866,419 A | 2/1999 | Meder | 435/394 |
| 5,924,583 A | 7/1999 | Stevens et al. | 215/40 |
| 5,935,847 A * | 8/1999 | Smith et al. | 435/297.5 |
| 6,001,642 A | 12/1999 | Tsao | 435/297.3 |
| 6,066,497 A | 5/2000 | Powell | 435/298.2 |
| 6,150,159 A | 11/2000 | Fry | 435/304.1 |

* cited by examiner

Primary Examiner—David A. Redding
(74) Attorney, Agent, or Firm—Shook, Hardy & Bacon, L.L.P.

(57) ABSTRACT

A vessel for growing tissues, cells, microorganisms and the like is provided. The vessel includes a body, which defines an interior chamber, and at least one aperture in the body for permitting fluid communication between the interior chamber and the external environment. The body includes top and bottom walls each having a generally planar portion and a tapered portion. The tapered portion of the top wall tapers outwardly and downwardly from the planar portion thereof to an outer periphery. Conversely, the tapered portion of the bottom wall tapers outwardly and upwardly from the planar portion thereof to an outer periphery. The outer peripheries of the respective walls are then aligned with and coupled to one another. The aperture includes a closure component coupled thereto for closing off the interior chamber from the external environment. In an alternative embodiment, the vessel includes a top wall, a bottom wall and at least one side wall. The side wall is coupled to each of the top and bottom walls to define an interior chamber.

18 Claims, 1 Drawing Sheet

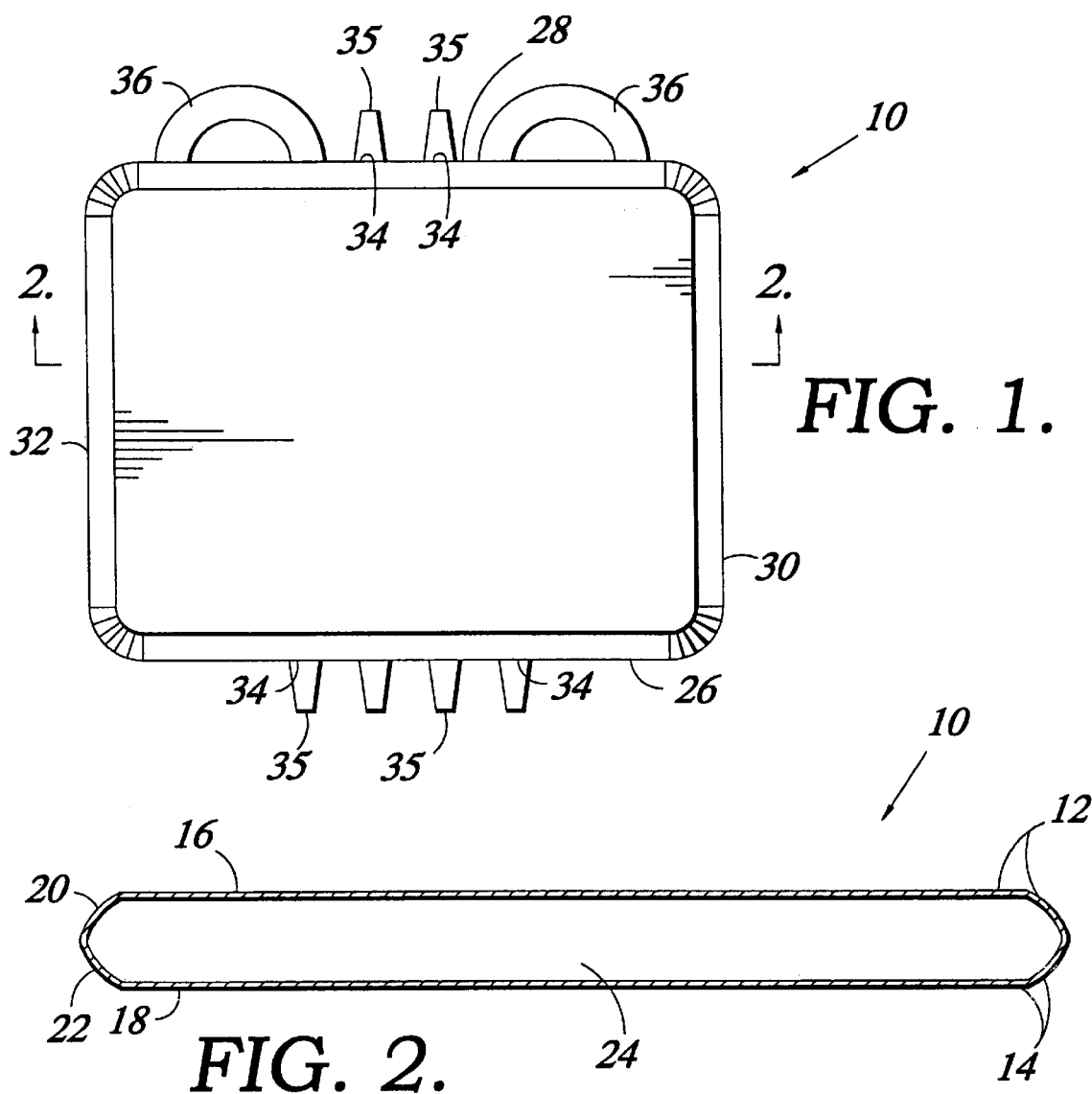
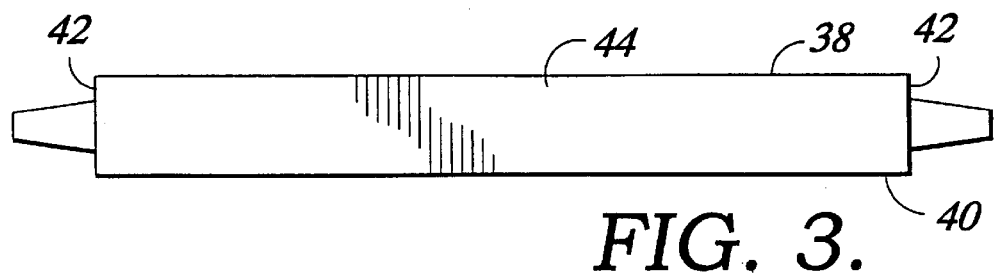

CELL CULTURE VESSEL

STATEMENT REGARDING FEDERALLY SPONSORED RESEARCH OR DEVELOPMENT

Not Applicable.

CROSS-REFERENCE TO RELATED APPLICATIONS

Not Applicable.

BACKGROUND OF THE INVENTION

This invention relates generally to the field of laboratory vessels. More specifically, this invention relates to a laboratory container or vessel for the culturing of tissues, cells, microorganisms and the like that maximizes the fluid phase and solid surface growing area by excluding gaseous interchange with the external environment.

Specialized vessels or containers, known generally as cell culture vessels, are used in the laboratory for a variety of purposes. Typically, however, such containers are used to grow rapidly multiplying cells in a culture medium or agar, either in fluid phase or adhered to an interior surface of the container. Types of such specialized vessels include non-static vessels, such as roller bottles and spinner flasks, as well as static vessels, such as petri dishes and tissue flasks. Roller bottles are containers which may be placed into a machine to gently agitate the contents thereof and to provide a continuous bathing of cells growing therein. Spinner flasks are designed to similarly agitate their contents through use of a moving paddle which continuously suspends cellular material in the culture medium. Static vessels, on the other hand, are designed such that their contents are not agitated but rather remain relatively static.

Each of the above types of vessels is designed to be incubated in temperature, humidity and gas controlled environments to facilitate maximum cell or tissue growth. Generally, a layer of cell culture medium or agar covers the growing surface. The portion of the vessel not utilized as a growing surface encloses the interior gaseous environment which surrounds the cell culture.

Cells, tissues, microorganisms and the like typically are introduced into the interior of cell culture vessels through an opening in the vessel. After introduction, the opening may be capped as desired such that the interior of the vessel is closed to the external environment. A cell culture vessel which is standard in the art is disclosed in U.S. Pat. No. 5,924,583. The '583 patent discloses a plastic cell culture vessel having a wide neck which has an opening at one end thereof. The opening opens to the external environment and facilitates access to the interior of the vessel. A screw cap is adapted to close off the opening when such access is no longer desired.

Conventional vessel designs such as those discussed above expose the growing cells to $O_2$ in the external environment. A steady source of environmental $O_2$ is believed to be important for healthy cell growth. It is difficult, however, to control the pH of the culture medium in such conditions. Therefore, it is generally believed to be necessary to grow cells in the presence of $CO_2$ in order to maintain the medium in a pH range that is optimal for cell growth. Despite the generally accepted belief regarding the importance of environmental $O_2$ for cell growth, there is a growing body of evidence that this underlying assumption is incorrect and, in fact, the amount of $O_2$ dissolved in the culture medium itself is sufficient to sustain cell growth to relatively high densities. Additionally, studies indicate that pH may be maintained through use of Hepes buffer.

The types of vessels described above suffer from a number of drawbacks. First, non-static vessels are generally fairly labor intensive requiring frequent monitoring of the agitation of their contents. Secondly, both non-static and static type devices are typically unreliable for the maintenance of sterility. It is standard belief in the art that it is desirable to have a cell culture vessel with an access opening or port that is sufficiently large to permit access to the entire bottom surface of the vessel. This allows cells to be harvested from the vessel walls and minimizes interference upon pouring from the vessel cells that have been cultured therein. Further, desired gas interchange between the internal environment and the external environment of the vessel occurs through the opening in the vessel when the cap is loosened or removed. Vessel designs having such a large access port generally are referred to as "open", indicating that they must be opened at some time during use to allow access and/or gaseous interchange. However, this type of direct gaseous communication with the ambient environment, creates the possibility of bacterial contamination and renders these systems unreliable for maintaining aseptic or sterile conditions. When contamination with ambient elements occurs, the contents of the vessel must be rejected, thereby causing a significant loss of data and time.

Another drawback of the cell culture vessels discussed above is that the vessels often do not maximize use of laboratory space. In laboratory practice, it is quite common to arrange or stack several cell culture vessels in a single chamber, such as an incubator, to maximize the use of available space. The shape of individual vessels is crucial with regard to the number of vessels which may be positioned in a single chamber. However, the shape of many of the cell culture vessels described above renders them difficult to stack. Accordingly, these vessels fail to maximize the use of the available space in laboratory chambers.

Despite these drawbacks, little effort has been devoted to the development of cell culture vessels that are designed to grow cells in either a pure fluid phase or solid surface environment which eliminates gaseous interchange with the external environment, although such a vessel would dramatically decrease sterility concerns. There are notable exceptions, however. For instance, one alternative to plastic culture vessels are gas permeable plastic bags such as those disclosed in U.S. Pat. Nos. 3,941,662, 4,142,940 and 4,829,002. Additionally, fermentation vessels that were previously used for microbial culture have been adapted for cell growth. Further, various cell culture systems have been developed that employ hollow fiber cartridges for cell growth. Fiber cartridge systems typically include a housing and a plurality of capillaries or hollow fiber membranes which contain selectively permeable walls through which cell culture media may diffuse. Examples of such systems are disclosed in U.S. Pat. Nos. 5,763,261, 5,424,209 and 4,889,812.

Each of these alternative culture vessels has been developed to fill a specific niche that could not be satisfied by the conventional plastic culture vessels typically used in the art. Unfortunately, however, most of the advantages that are provided in the simple, flat-surfaced plastic cell culture vessels are lost when the vessels are modified in any one of the above-listed ways.

Accordingly, there is a continuing need in the cell culture industry for an improved cell culture vessel which produces increased cell growth efficiency. Additionally, there remains a need for a modified cell culture vessel that maximizes the fluid phase and solid surface growing area by excluding gaseous interchange with the external environment while maintaining the advantages provided by flat-surfaced plastic cell culture vessels. Further, there is a need for a cell culture vessel that allows simple, inexpensive, large-scale anchorage dependent culture of tissues, cells and/or microorganisms, either in fluid phase or adhered to the interior surface of the container, which is of a shape conducive to stacking one upon another.

SUMMARY OF THE INVENTION

Accordingly, in one of its aspects, the present invention provides an improved cell culture vessel having quality construction for culturing cells, tissues, microorganisms and the like.

In a further aspect, the present invention provides a cell culture vessel which produces increased cell growth efficiency.

In another of its aspects the invention provides a cell culture vessel which maximizes fluid phase and solid surface growing area as it may be completely filled with culture medium.

In still another of its aspects, the present invention provides a cell culture vessel that is designed to allow medium and cells or tissues to be added or removed while simultaneously excluding the external gaseous environment.

In yet another of its aspects, the present invention provides a cell culture vessel which eliminates the need to grow cells in $CO_2$ incubators to maintain gas and humidity control.

In a still further aspect, the present invention provides a cell culture vessel of a shape which maximizes use of laboratory space by permitting a plurality of vessels to be stacked upon one another.

According to the present invention, the foregoing and other objects are achieved by a vessel for growing tissues, cells and/or microorganisms which comprises a body defining an interior chamber and at least one aperture in the body for permitting fluid communication between the interior chamber and an external environment. The body includes top and bottom walls each having a planar portion and a tapered portion. The tapered portion of the top wall tapers outwardly and downwardly from the planar portion thereof to define an outer periphery. The tapered portion of the bottom wall tapers outwardly and upwardly from the planar portion thereof to define an outer periphery. The outer peripheries of the respective walls are aligned with and coupled to one another. The aperture includes a closure component coupled thereto for closing off the interior chamber from the external environment.

The present invention further provides a cell culture vessel having a body which defines an interior chamber and at least one aperture in the body for permitting fluid communication between the interior chamber and an external environment. The body includes spatially removed first and second body walls and at least one side wall. The first and second body walls are generally planar and are substantially parallel to one another with each body wall defining an outer periphery thereof. The side wall has a top edge and a bottom edge and is positioned such that the top edge aligns with the outer periphery of the first body wall and is coupled thereto and the bottom edge aligns with the outer periphery of the second body wall and is coupled thereto. The aperture in the body includes a closure component coupled thereto for closing off the interior chamber from the external environment.

Additional aspects of invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means, instrumentalities and combinations particularly pointed out in the appended claims.

BRIEF DESCRIPTION OF THE DRAWINGS

In the accompanying drawings which form a part of the specification and are to be read in conjunction therewith and in which like reference numerals are employed to indicate like parts in the various views:

FIG. 1 is atop perspective view of a cell culture vessel constructed in accordance with a first preferred embodiment of the present invention;

FIG. 2 is a cross-sectional view taken along line 2—2 of FIG. 1 in the direction of the arrows; and FIG. 3 is a side view of a cell culture vessel constructed in accordance with a second preferred embodiment of the present invention.

DETAILED DESCRIPTION OF THE SEVERAL VIEWS OF THE DRAWINGS

The present invention is directed to a cell culture vessel for the culturing of tissues, cells and microorganisms that maximizes the fluid phase and solid surface growing area by excluding gaseous interchange with the external environment. The particular embodiments described herein are intended in all respects to be illustrative rather than restrictive. Alternative embodiments will become apparent to those skilled in the art to which the present invention pertains without departing from its scope.

Referring to the drawings in general and initially to FIGS. 1 and 2 in particular, wherein like reference numerals identify like elements in the various views, a cell culture vessel manifesting aspects of the present invention is illustrated therein and is designated generally by the numeral 10. In a preferred embodiment, vessel 10 is generally rectangular in shape and may be formed of any suitable material, e.g., molded transparent plastic. Preferably, vessel 10 is formed of polystyrene. Vessel 10 includes a top wall 12 and a bottom wall 14 which collectively comprise the body of the vessel. The interior surface of each of the top wall 12 and the bottom wall 14 define growing zones for cells, i.e., both interior surfaces may accommodate a cell culture medium.

Each of the top wall 12 and the bottom wall 14 include a planar portion, 16, 18 respectively, and a tapered portion, 20, 22 respectively. Planar portions 16, 18 are spatially removed from one another and are generally parallel. As illustrated in FIG. 2, the tapered portion 20 of top wall 12 is disposed at a downwardly and outwardly inclined angle with respect to the planar portion 16 of the top wall. The tapered portion 22 of bottom wall 14 is disposed at an upwardly and outwardly inclined angle with respect to the planar portion 18 of the bottom wall. Each tapered portion defines an outer periphery thereof (not shown). Top wall 12 and bottom wall 14 are aligned with one another such that the respective tapered portions taper toward one another and align at their outer peripheries. When aligned in this manner, vessel 10 defines an interior chamber 24 which is completely enclosed by the vessel body. The outer peripheries of top wall 12 and bottom wall 14 may be coupled by any well-known bonding technique, such as, for example, ultrasonic welding or the like. In a preferred embodiment, the outer peripheries of the two walls 12, 14 are molded as an integral unit.

In the preferred embodiment, vessel 10 is generally rectangular in shape with rounded corners and includes first and second longitudinal edges and first and second lateral edges. In one preferred embodiment, the first and second lateral edges are approximately twelve inches in length and the first and second longitudinal edges are approximately fifteen inches in length. This embodiment permits four vessels to be positioned adjacent one another on a single shelf of a Forma Model 3956 incubator. In a second preferred embodiment, the first and second lateral edges are approximately seventeen inches in length and the first and second longitudinal edges are, likewise, seventeen inches in length. This alternative embodiment permits a single vessel to be positioned on the surface of many known $CO_2$ incubators which are smaller in size, e.g., a Forma Model 3326 incubator. The dimensions of each of these embodiments is preferred based upon the dimensions of well-known and widely utilized incubating chambers. It will be understood and appreciated, however, that a vessel having any number of shapes or dimensions is contemplated within the scope of the present invention.

As stated above, top wall 12 and bottom wall 14 preferably are formed of a molded, transparent material such as polystyrene. In the preferred embodiment, both the top and bottom walls 12, 14 have optical characteristics that permit distortion-free viewing of the tissues, cells, and/or microorganisms growing on the inner surface of the walls. Further, it is preferred that at least one of the top or bottom walls 12, 14 is frosted on at least a portion thereof to facilitate labeling of the vessel.

While in FIG. 2 the point at which the outer peripheries of the top and bottom walls are coupled, i.e., the coupling point, is shown to be equidistant from the respective planar portions of the two walls, the coupling point may be located more proximate one wall than the other as desired. Such variation is contemplated to be within the scope of the present invention. In the embodiment wherein the coupling point is equidistant from each planar portion, 16, 18, the vessel may be formed of two identical walls, formed from a single mold, and positioned with respect to one another to define an interior chamber 24 as shown.

As best illustrated in FIG. 1, the interior chamber 24 of vessel 10 is accessible through a number of apertures or ports 34 which are disposed on the vessel body at or near the coupling point of the top and bottom walls 12, 14. Each port may be an inlet into the interior chamber or an outlet therefrom as desired. In the preferred embodiment, vessel 10 includes a total of six ports, four located along the first longitudinal edge 26 of the vessel and two located along the opposing longitudinal edge 28. Ports 34 are preferably of standard size in the art so that each is able to be fitted with one of a variety of commercially available adaptors which permit cells, cell culture medium or other materials to be injected into the interior chamber 24 without compromising internal integrity. In the preferred embodiment, each port is fitted with either a male or female Luer adaptor 35.

In the preferred embodiment, two of the ports located along the first longitudinal edge 26 of the vessel 10, are fitted with male Luer adaptors 35 and thus permit cells or additives to be injected into the interior chamber. One of the remaining two ports 34 located along the first longitudinal edge 26 of the vessel 10 is fitted with a female Luer adaptor which permits medium and cell removal from the interior chamber 24 of the vessel. The remaining port 34 on the first longitudinal edge 26 is fitted with a Luer adaptor 35 which permits the port to be connected to a pump for continuous medium flow. One of the two ports 34 located on the second longitudinal edge 28 is fitted with a male Luer adaptor 35 which permits air to be taken in simultaneously with medium withdrawal. The other of the two ports 24 located on the second longitudinal edge 28 is fitted with a Luer connector 35 that permits the port to be connected to a pump for continuous medium flow.

It will be understood and appreciated that the described arrangement of six ports is the preferred embodiment of this design. However, any number of ports and any combination of connectors and adaptors may be utilized as desired. Such modifications are contemplated to be within the scope of the present invention. The arrangement illustrated herein is merely exemplary and is not intended to limit the scope of the present invention. One particularly contemplated modification involves a port having a cap which contains a gas permeable, liquid permeable membrane and thus permits gas interchange with the external environment as desired.

Returning to FIG. 1, vessel 10 further may include one or more handles 36 to facilitate transport and positioning of the vessel. In the preferred embodiment, handles 36 are secured to the second longitudinal edge 28 of vessel 10 as this particular edge has fewer ports included thereon. It will be understood and appreciated, however, that the handles 36 may be secured to vessel 10 at any location as desired. Alternatively, vessel 10 may be manufactured without handles. Such alternative embodiments are contemplated to be within the scope of the present invention. Preferably, handles 36 are formed from the same molded, transparent plastic material as the body of the vessel 10. However, handles 36 may be formed from any suitable material that would permit secure attachment to the body of the vessel 10. For example, handles 36 may be made from plastic having more flexibility than the body of the vessel. Such variations are contemplated to be within the scope of the present invention.

The volume of the interior chamber 24 depends upon the distance of separation between the respective planar portions 16, 18 of top wall 12 and bottom wall 14 as well as the inclination angles of tapered portions 20, 22. While this distance of separation may be any desired distance to accommodate varying volumes of cell culture medium as desired, in the preferred embodiment, the vessel is designed to allow the cells to be bathed in at least the amount of medium in which they would be bathed in currently available cell culture vessels. Such volumes vary based upon the type of cell culture desired and the standard volumes are well known to those skilled in the art. In the preferred embodiment, the distance of separation between the respective planar portions 16, 18 of top wall 12 and bottom wall 14 is between approximately ¼ inch and ¾ inch, preferably approximately ⅜ inch. In the present invention, the volume of the interior chamber 24 may closely approximate the volume of culture medium desired as the vessel 10 is designed such that the interior chamber may be completely filled with medium.

In an alternate embodiment, illustrated in FIG. 3, cell culture vessel 10 includes a first body wall 38, a second body wall 40 and at least one side wall 42. Collectively the walls comprise the body of the vessel. First and second body walls 38, 40 are generally planar and are substantially parallel to one another. Further, first body wall 38 and second body wall 40 are spatially removed from one another by a distance equal to the height of side wall 42. Each of first body wall 38 and second body wall 40 define outer peripheries thereof.

Side wall 42 includes a top edge and a bottom edge. In the preferred embodiment, side wall 42 is between approximately ¼ inch and approximately ¾ inch, preferably approximately ⅜ inch, in height. The top edge of side wall 42 is coupled to the outer periphery of first body wall 38. The bottom edge of side wall 42 is coupled to the outer periphery 46 of second body wall 40. Side wall 42 may be coupled to the first body wall 38 and the second body wall 40 by any means known in the art, e.g., ultrasonic welding or the like, and such is contemplated to be within the scope of the present invention. It is further contemplated that varying heights of side wall 42 may comprise the present invention and such is intended within the scope hereof. Side wall 42 may be a continuous, single wall or a number of wall portions coupled together at their respective lateral edges. Such variations are contemplated to be within the scope of the present invention.

In order to permit access to the interior chamber 44 of vessel 10, a number of ports or openings (not shown) are provided which are disposed in side wall 42 in a manner as discussed above with regard to the first preferred embodiment. Further, the alternate embodiment of FIG. 3 may include one or more handles (not shown) disposed as discussed above.

In operation, culture medium or agar is injected into the cell culture vessel of the present invention through one or more of the ports in the vessel body. The interior chamber of the vessel may be partially or completely filled with medium as desired. Cells, tissues, microorganisms or the like may be similarly injected without exposing the interior chamber to the external gaseous environment. Subsequently, a plurality of the vessels may be inserted into an incubator chamber as desired for growing. As the culture medium is not exposed to the external environment, it is not necessary that humidity and gas be controlled to facilitate maximum cell or tissue growth. Rather, a temperature-controlled incubator, e.g., a 37° C. temperature incubator, may be used. If desired, the vessels may be stacked one upon another as the substantially flat top and bottom walls facilitate such positioning within the incubating chamber.

Constructed and operated as previously described, the present invention provides a cell culture vessel which may be partially or completely filled with culture medium or agar as desired through one or more of the ports in the vessel body. Thus, both fluid phase and solid surface growing area are maximized. Further, as the interior chamber of the vessel is completely enclosed, gaseous interchange with the external environment is eliminated. As a result, sterility concerns are significantly diminished in comparison with prior art vessels. Additionally, as the vessel of the present invention has a relatively flat shape and a minimum height necessary for cell growth, a plurality of vessels may be stacked upon one another maximizing use of laboratory space.

In an alternative embodiment, to further facilitate stable stacking of multiple vessels atop one another, interlocking plastic members may project from one or more surfaces of vessel 10. Such projecting members aid in preventing the vessels from sliding off of one another upon stacking. Such variation is contemplated to be within the scope of the present invention.

A single tissue culture vessel has been described herein. It will be understood and appreciated, however, that the concepts and construction described above may be utilized in a multi-layer cell culture unit. Such a unit may permit access to and from the unit as a whole or to and from particular individual layers of the unit. Such a multi-layer design would be beneficial for large-scale tissue culture operations and is contemplated to be within the scope of the present invention.

In conclusion, the present invention is directed to a cell culture vessel for the culturing of tissues, cells and microorganisms that maximizes the fluid phase and solid surface growing area by excluding gaseous interchange with the external environment. The present invention has been described in relation to particular embodiments which are intended in all respects to be illustrative rather than restrictive. Alternative embodiments will become apparent to those skilled in the art to which the present invention pertains without departing from its scope.

From the foregoing, it will be seen that this invention is one well adapted to attain all the ends and objects hereinabove set forth together with other advantages which are obvious and which are inherent to the vessel structure.

It will be understood that certain features and subcombinations are of utility and may be employed without reference to other features and subcombinations. This is contemplated by and is within the scope of the claims.

Having thus described the invention, what is claimed is:

1. A cell culture vessel, said vessel comprising:

a gas impermeable body defining an interior chamber, wherein said body includes a top wall and a bottom wall, each said wall having a planar portion and a tapered portion, wherein said tapered portion of said top wall tapers outwardly and downwardly from said planar portion of said top wall and said tapered portion of said bottom wall tapers outwardly and upwardly from said planar portion of said bottom wall, and wherein said top and bottom walls are positioned such that said planar portions are substantially parallel to one another and said tapered portions align and are coupled to one another at respective outer peripheries thereof; and at least one aperture in said body for permitting fluid communication between said interior chamber and an external environment, said aperture permitting substantially no gaseous interchange with the external environment.

2. The cell culture vessel as recited in claim 1, wherein said aperture includes a closure component coupled thereto for closing off said interior chamber from said external environment.

3. The cell culture vessel as recited in claim 1, wherein said top wall and said bottom wall are integrally formed.

4. The cell culture vessel as recited in claim 1, wherein said vessel is formed of a transparent plastic material.

5. The cell culture vessel as recited in claim 4, wherein said transparent plastic material is polystyrene.

6. The cell culture vessel as recited in claim 1, wherein at least one of said top and bottom walls is frosted on at least a portion thereof for facilitating labeling of the vessel.

7. The cell culture vessel as recited in claim 1, wherein said body is substantially rectangular in shape.

8. The cell culture vessel as recited in claim 1, further comprising at least one handle extending from said body, said handle facilitating transport and positioning of the vessel.

9. A laboratory vessel for growing tissues, cells and microorganisms, said vessel comprising:

a gas impermeable body defining an interior chamber, wherein said body includes
spatially removed first and second body walls, wherein said body walls are generally planar and are substantially parallel to one another, each said body wall defining an outer periphery thereof, and at least one side wall, said side wall having a top edge and a bottom edge, wherein said side wall is positioned such that said top edge aligns with said outer periphery of said first body wall and is coupled thereto and said bottom edge aligns with said outer periphery of said second body wall and is coupled thereto; and at least one aperture in said body for permitting fluid communication between said interior chamber and an external environment, said aperture permitting substantially no gaseous interchange with the external environment.

10. The laboratory vessel as recited in claim 9, wherein said aperture includes a closure component coupled thereto for closing off said interior chamber from said external environment.

11. The laboratory vessel as recited in claim 9, wherein each said body wall and said side wall are integrally formed.

12. The laboratory vessel as recited in claim 9, wherein said vessel is formed of a transparent plastic material.

13. The laboratory vessel as recited in claim 12, wherein said transparent plastic material is polystyrene.

14. The laboratory vessel as recited in claim 9, wherein at least one of said body walls is frosted on at least a portion thereof for facilitating labeling of the vessel.

15. The laboratory vessel as recited in claim 9, wherein said body is substantially rectangular in shape.

16. The laboratory vessel as recited in claim 9, further comprising at least one handle extending from said body, said handle facilitating transport and positioning of the vessel.

17. The cell culture vessel as recited in claim 1, wherein said aperture is formed in said tapered portion.

18. The laboratory vessel as recited in claim 9, wherein said aperture is formed in said sidewall.

* * * * *